US009024902B2

(12) United States Patent
Varna

(10) Patent No.: US 9,024,902 B2
(45) Date of Patent: May 5, 2015

(54) ULTRASOUND DEVICE AND METHOD THEREOF

(71) Applicant: General Electric Company, Schenectady, NY (US)

(72) Inventor: Srinivas Varna, Bangalore (IN)

(73) Assignee: General Electric Company, Schenectady, NY (US)

( * ) Notice: Subject to any disclaimer, the term of this patent is extended or adjusted under 35 U.S.C. 154(b) by 38 days.

(21) Appl. No.: 13/849,911

(22) Filed: Mar. 25, 2013

(65) Prior Publication Data

US 2013/0249842 A1 Sep. 26, 2013

(30) Foreign Application Priority Data

Mar. 26, 2012 (IN) .......................... 1136/CHE/2012

(51) Int. Cl.
| | | |
|---|---|---|
| G09G 5/00 | (2006.01) | |
| G06F 3/041 | (2006.01) | |
| G06F 3/0488 | (2013.01) | |
| G06F 3/0484 | (2013.01) | |
| A61B 8/00 | (2006.01) | |

(52) U.S. Cl.
CPC ............ *G06F 3/041* (2013.01); *G06F 3/04886* (2013.01); *G06F 3/04847* (2013.01); *A61B 8/467* (2013.01)

(58) Field of Classification Search
CPC . G06F 3/041; G06F 3/04886; G06F 3/04847; A61B 8/00; A61B 8/52; A61B 8/5207; A61B 2562/0204; A61B 8/467; G01S 7/52036; G01S 7/52084; G06T 2207/10132; G06T 2207/30004
USPC .................. 345/173; 600/437, 443, 458, 463; 382/128; 128/916
See application file for complete search history.

(56) References Cited

U.S. PATENT DOCUMENTS

| | | | | |
|---|---|---|---|---|
| 6,063,030 | A | * | 5/2000 | Vara et al. ..................... 600/437 |
| 2004/0015079 | A1 | * | 1/2004 | Berger et al. ................. 600/437 |
| 2008/0208047 | A1 | * | 8/2008 | Delso ............................ 600/437 |
| 2010/0049051 | A1 | | 2/2010 | Sang et al. |
| 2010/0094132 | A1 | * | 4/2010 | Hansen et al. ................ 600/443 |
| 2010/0145195 | A1 | * | 6/2010 | Hyun ............................ 600/437 |
| 2012/0065508 | A1 | * | 3/2012 | Gerard et al. ................. 600/443 |
| 2012/0179039 | A1 | * | 7/2012 | Pelissier et al. .............. 600/443 |
| 2013/0064036 | A1 | * | 3/2013 | Lee et al. .......................... 367/7 |

* cited by examiner

*Primary Examiner* — Tom Sheng
(74) *Attorney, Agent, or Firm* — GE Global Patent Operation; Marc A. Vivenzio

(57) ABSTRACT

Embodiments of the present invention relate to a Time Gain Compenstaion (TGC) feature in an ultrasound device using a touchpad or similar device, which eliminates the need for mechanical potentiometers. The touchpad is segmented into one or more rows, wherein each row is mapped to a corresponding depth of an image. In order to set a required TGC gain setting of a particular depth of the image, a user moves his/her finger across the face of the touchpad such that the desired gain curve can be set. Finer adjustments can be done by moving the finger in the desired horizontal area of the touchpad. The mapping of the effective depths is indicated by horizontal lines on the touchpad as well as on the screen.

9 Claims, 5 Drawing Sheets

ULTRASOUND DEVICE AND METHOD THEREOF

BACKGROUND OF THE INVENTION

Embodiments of the present invention relate to a medical device. Further, the embodiments of the present invention relate to an ultrasound device comprising a touchpad segmented into one or more rows or similar kind of touchpad devices.

Traditional potentiometers present in existing ultrasound devices are vulnerable to liquid, dust, and gel ingress. An example of an existing ultrasound device, as illustrated in FIG. 1A, uses functionality of a trackball and Time Gain Compensation (TGC) potentiometers resulting in high cost and a complex system. With traditional TGC implementations, the number of regions that can be controlled is limited by the number of potentiometers. It's very hard to implement and memorize several different TGC settings for different applications without physically moving the mechanical potentiometers in the existing ultrasound systems.

Hence, there exists a need for an ultrasound device that overcomes the drawbacks of the existing systems and also improves the implementation of TGC functionality corresponding to different applications to provide more accurate adjustments of an ultrasound image as per the requirement by a user.

BRIEF DESCRIPTION OF THE INVENTION

An ultrasound device comprising an input unit and a display unit is described herein. In an embodiment, the input unit comprising a touchpad with multi-touch support segmented into at least one row. Each row is mapped to a corresponding depth of an image formed based on echoed signals of an object, and received through an ultrasound probe. The touchpad enables or facilitates a user to adjust a gain of the image using a Time Gain Compensation (TGC) function implemented in a processor associated with the ultrasound device. The display unit comprising at least one predetermined marking corresponding to at least one row which is segmented on the touch pad. The marking indicates corresponding depth of the image being adjusted by the user using at least one row of the touchpad.

In another embodiment, a method of processing an image using an ultrasound device is disclosed. The method comprises receiving echoed signals of an object through an ultrasound probe by a processor, forming an image based on the echoed signals of the object, computing depths of the image before displaying on a display unit by the processor, and mapping the depths of the image to one or more corresponding rows formed on a touchpad. The touchpad facilitates a user to adjust gain the image using a Time Gain Compensation function implemented in the processor.

BRIEF DESCRIPTION OF THE DRAWINGS

Embodiments of the present invention are set forth with particularity in the appended claims. The disclosure itself, together with further features and attended advantages, will become apparent from consideration of the following detailed description, taken in conjunction with the accompanying drawings. One or more embodiments of the present disclosure are now described, by way of example only, with reference to the accompanied drawings wherein like reference numerals represent like elements and in which:

Figure 1A:
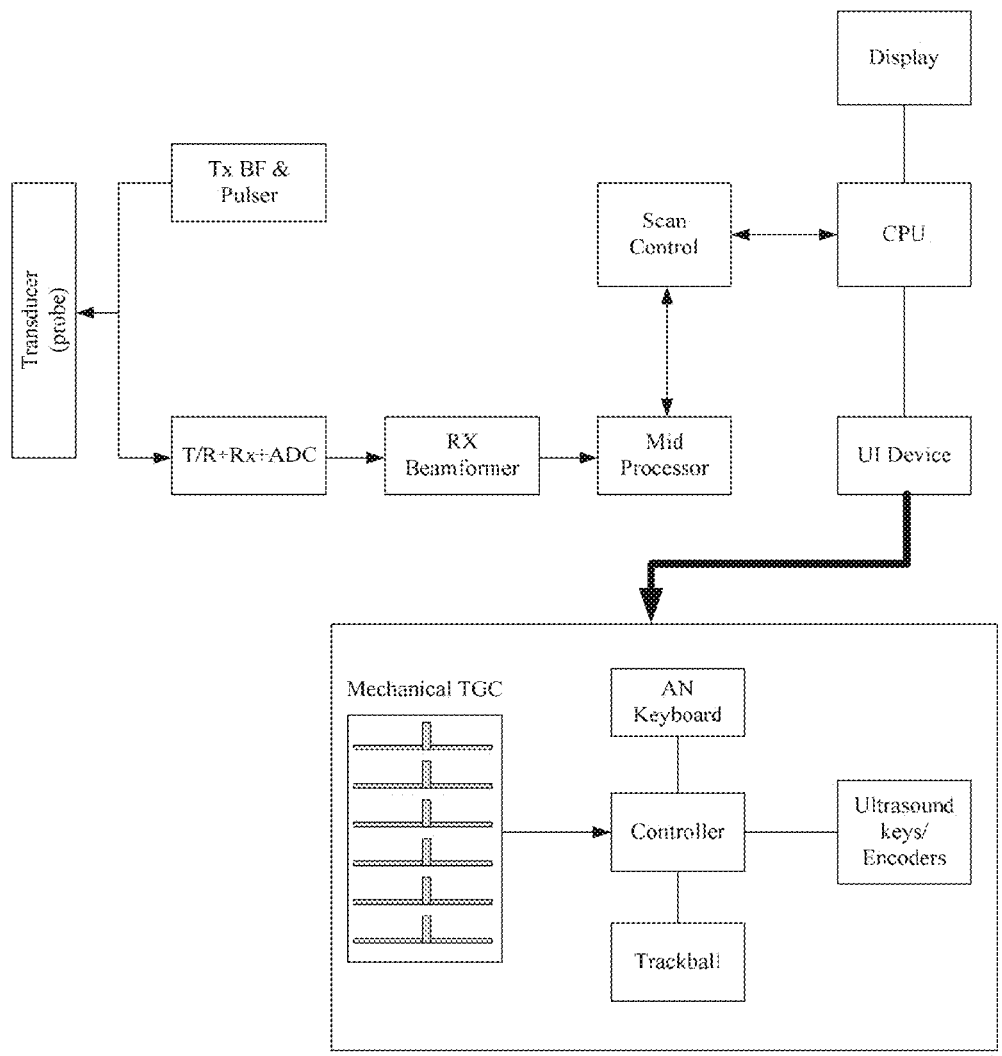
FIG. 1A illustrates a block diagram of an existing ultrasound device comprising potentiometers to implement Time Gain Compensation (TGC) function according to an embodiment of the present invention.

The figures depict embodiments of the invention for purposes of illustration only. One skilled in the art will readily recognize from the following description that alternative embodiments of the structures and methods illustrated herein may be employed without departing from the principles of the disclosure described herein.

DETAILED DESCRIPTION OF THE INVENTION

The foregoing has broadly outlined the features and technical advantages of the present invention in order that the detailed description of the disclosure that follows may be better understood. Additional features and advantages of the disclosure will be described hereinafter which support the claims of the disclosure. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

An ultrasound device is disclosed as an embodiment of the present invention. The ultrasound device comprises an input unit and a display unit. The input unit comprises a touchpad. The touchpad is segmented into one or more rows. Each row is mapped to a corresponding depth of an image formed based on echoed signals of an object received through an ultrasound probe. The touchpad facilitates a user to adjust gain of the image using a Time Gain Compensation (TGC) function implemented in a processor associated with the ultrasound device. The display unit comprises at least one predetermined marking corresponding to one or more rows segmented on the touchpad. These markings on the display unit indicate corresponding depths of the image being adjusted by the user using the one or more rows of the touchpad. The predetermined depths of the displayed image are in the range of approximately 1 centimeter to 30 centimeters. Here, the depths of the image are a representation of the received echoed signals on the display unit. More particularly, when the electric signals encounter a material or human body with a different density (acoustic impedance), part of the signals is reflected back to the probe and is detected as an echo. The time it takes for the echo to travel back to the probe is measured and used to calculate the depth of the tissue interface causing the echo. Therefore, the depths of the image are the density of the electric signals reflected from the human body.

However, the different depths of the human body can be measured depending on the different frequencies of the electric signals transmitted to the human body. The depth of the image involves adjustment of the gain of the image to be adjusted by implementing TGC settings. Specifically, the TGC settings rely upon the gains of the image being adjusted selectively at different depths. This adjustment may accommodate both close and far afield on some portables. This compensates for distortion caused by superficial tissue. The adjustments are most effective when examining an area. When examining relatively small specific structures such as, for example, a shoulder, adjustment of the overall gain is usually sufficient. If the gain of the image is brightness, which is adjusted by implementing TGC settings, a finger is moved across the touchpad using multi-touch to adjust the brightness of the image. The gain of the desired depth of the image is adjusted by sliding at least a finger or a stylus across (e.g. horizontally) on the row of the touchpad, mapped correspondingly to the desired depth of the image implementing the TGC settings.

A method of processing an image using an ultrasound device is disclosed as an embodiment of the present invention. The method comprises receiving echoed signals of an object through an ultrasound probe by a processor and forming an image based on echoed signals of the object. The object is selected from at least one of a human body and an animal body. Then, depths of the image before displaying on a display unit are computed by the processor. After computing the depth(s) of the image, the computed depth(s) of the image is/are mapped to one or more corresponding rows formed on the touchpad. The rows of the touchpad facilitate a user to adjust gain of the image using a Time Gain Compensation (TGC) function which is implemented in the processor. The gain of the image is adjusted by moving at least one of a finger and a stylus in a predefined direction on the touchpad. The shape of the applied TGC curve is displayed next to the image for reference which helps the user to adjust the depth(s) of the displayed image.

Figure 1B:
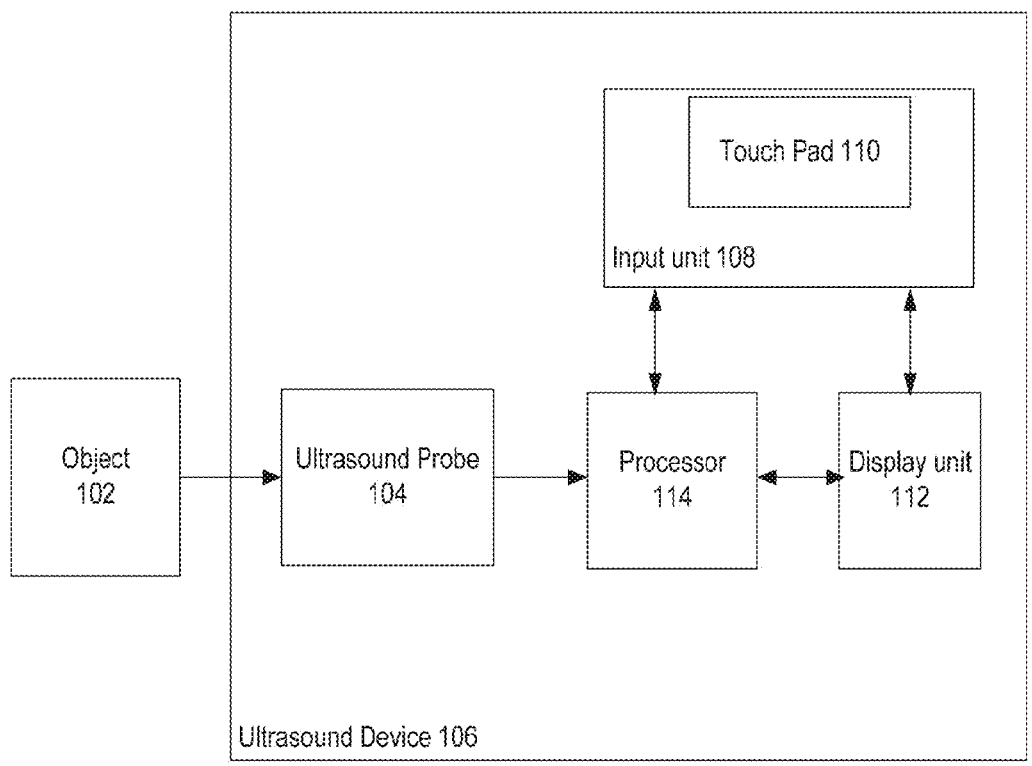
FIG. 1B illustrates a block diagram of an ultrasound device comprising a touchpad used to implement Time Gain Compensation (TGC) function in accordance with an embodiment of the present disclosure.

FIG. 1B illustrates a block diagram of an ultrasound device comprising an ultrasound probe 104, input unit 108 and display unit 112 to implement the TGC function according to an embodiment of the invention.

In FIG. 1B, the ultrasound probe 104 sends signals to the object 102 and receives echoed ultrasound signals from the object 102. The object 102 is selected from at least one of a human body and animal body. The echoed signals are processed by the processor 114 of the ultrasound device 106. The processed signals form the image and each depth of the image is mapped to the touchpad 110 and to the display unit 112. The touchpad 110 is used by the user (using a finger or stylus) to change the TGC gain curve of the image on the display unit 112. The input given by the user on the touchpad 110 is read by the processor 114 and the input is processed accordingly. The display unit 112 displays the image.

Figure 1C:
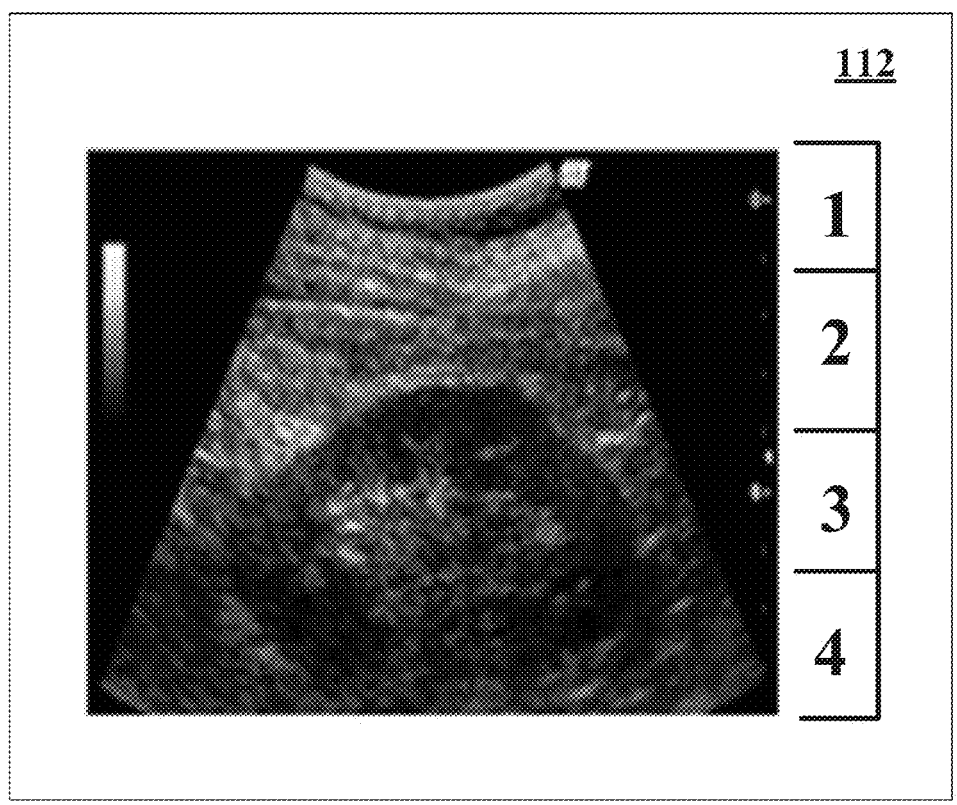
FIG. 1C shows an exemplary display unit showing image displayed on the display unit.

FIG. 1C shows an exemplary image with each depth displayed on the corresponding rows of a display unit 112 according to an embodiment of the present invention. The display unit 112, as shown in FIG. 1C, has one or more markings. For example, in FIG. 1C, these markings are numbered from marking 1 to marking 4. However, different types of markings or indicators can be provided on the display unit 112 to indicate the depth of the image.

In an embodiment, graphs corresponding to gain curves are on the display unit 112. Each of these markings corresponds to respective depths of the image. These depths are computed by the processor 114 of the ultrasound device when echoed signals of the object 102 are received by the probe 104. The depths of the image are adjusted by the user using the touchpad 110. With the help of the touchpad 110, the user can modify the depths of the image on the display unit 112. Further, a highlight can be made next to each marking to show that the particular depth of the image is being adjusted by the user. The highlight may include, but is not limited to, a color dot, a star, and an arrow. In an embodiment an audio member operable as a speaker is provided with the ultrasound device. A pre-recorded audio message can be played through the speaker to indicate particular depth of the image is being adjusted by the user.

Figure 1D:
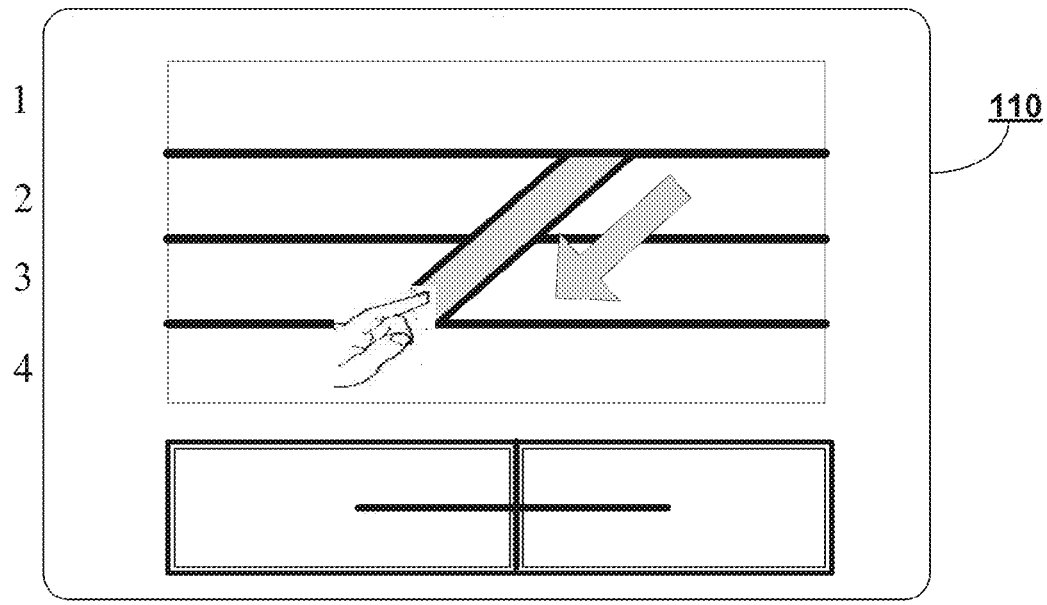
FIG. 1D depicts an exemplary touchpad used to set Time Gain Compensation (TGC) gain settings of the image displayed on the display unit in accordance with an embodiment of the present invention.
Figure 1E:
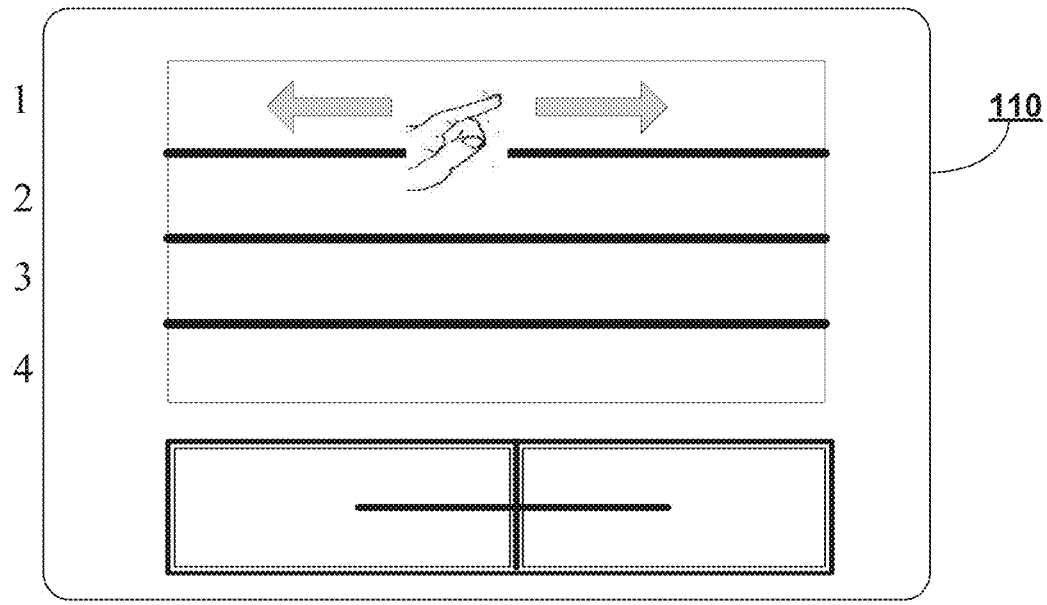
FIG. 1E depicts an exemplary touchpad used to set Time Gain Compensation (TGC) gain settings of the image displayed on the display unit in accordance with an embodiment of the present invention.

FIG. 1D and FIG. 1E depict an exemplary touchpad 110 used to set Time Gain Compensation (TGC) gain settings of the image displayed on the display unit 112 according to an embodiment of the present invention. The touchpad 110 is segmented into one or more horizontal rows corresponding to the depths of the image. The segmentation may be a virtual segmentation. In other words, the touchpad 110 is segmented in terms of pixels. A touchpad 110 is made up of pixels, and hence a predetermined number of pixels arranged in a row and selected in a segment line is drawn at the end of each row to differentiate individual depths of the image. For an example, number of pixels in the range of approximately 300 to 600 is selected to create each row on the touchpad 110. Further, number of pixels in each row can be varied based on the requirement and quality of the image. Since the leverage is given in selecting the number of pixels in each row, more number of rows can be created in the touchpad 110. This facilitates in accommodating more number of rows in a single touchpad 110. This type of arrangement eliminates the restriction posed in existing systems, which make use of mechanical potentiometers to adjust the depth(s) of the image. Thus, the number of depths of the image displayed is restricted in existing ultrasound devices as the number of potentiometers. In existing systems, the number of depths of the image to be displayed on the display screen is restricted to 12 or less. Alternatively, embodiments of the present invention display more than 12 depths of the image. Particularly, depths of the displayed image are approximately 1 centimeter to 30 centimeters. Since, touchpad 110 is used instead of mechanical potentiometers, this would result in increased resolution and helps in performing granular level adjustments on particular depth of the displayed image.

As further illustrated in FIG. 1D and FIG. 1E, each row of the touchpad 110 corresponds to respective depths of the image. For example, these rows are numbered in series from row 1 to row 4. The segmented rows on the touchpad 110 are used by the user to adjust the gain curves of the image displayed on the display unit 112. To adjust the gain curve, the user slides a finger or a stylus on the rows of the touchpad 110. Basically, the touchpad 110 is used to adjust the TGC settings of the image displayed on the display unit 112. The markings on the display unit 112 and rows of the touchpad 110 coincide with each other based on the depths of the image computed by the processor 114. For example, if the user desires to modify the depth of the image corresponding to marking 1, then the user slides row one (1) of the touchpad 110 to modify the depth of the image on the marking 1 of the display unit 112.

Referring back to FIG. 1D, if the brightness of the image is to be modified, then the gain curve shape of the image is manipulated by moving a finger or stylus across the touchpad using multi-touch. This modifies the TGC profile settings implemented for the image to be displayed on the corresponding markings of the display unit 112.

Referring back to FIG. 1E, if the user wants to perform finer adjustments on the displayed image, then the user needs to slide the associated row corresponding to the image depth required to be adjusted using a finger or a stylus.

Figure 2:
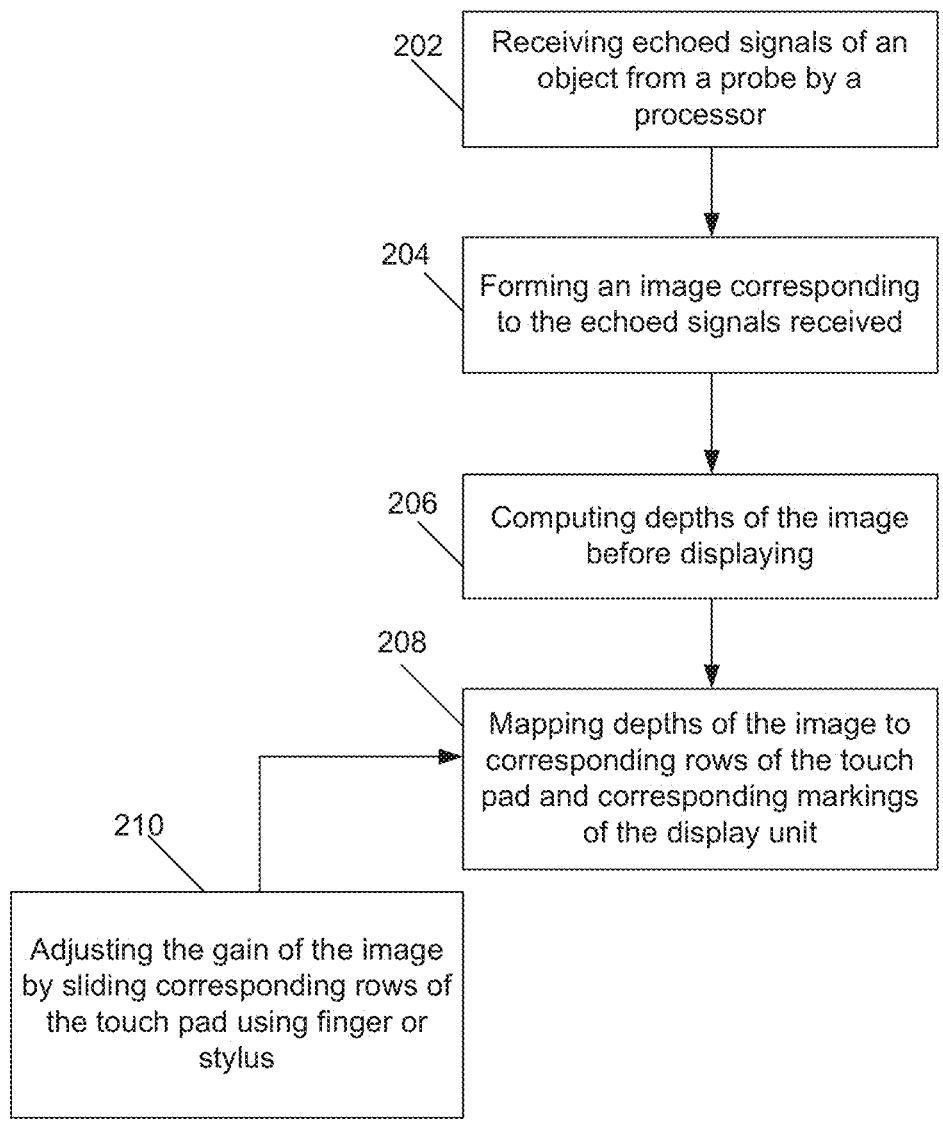
FIG. 2 illustrates exemplary logical steps used to map the depths of the image on the display unit and to adjust the TGC gain curves of the image in accordance with an embodiment of the present invention.

FIG. 2 illustrates exemplary logical steps used to map the depths of the image on the display unit 112 and to adjust the TGC gain curves of the image according to an embodiment of the present invention. FIG. 2 illustrates a method of processing an image using an ultrasound device. At step 202, the echoed signals of an object 102 are received by a processor 114 through an ultrasound probe 104. An image, before being displayed, is processed based on the echoed signals received by the ultrasound probe 104. The mapping of the image to the corresponding markings of the display unit 112 and to the corresponding segmented rows of the touchpad 110, as described at step 208, is achieved when the depths of the image are computed by the processor 114 at step 206. The rows of the touchpad facilitate a user to adjust gain of the image using the Time Gain Compensation (TGC) function which is being implemented in the processor 114. The gain of the image is adjusted by moving at least a finger or a stylus in a predefined direction on the touchpad, which is achieved at step 210. The shape of the applied TGC curve is displayed next to the image for reference which helps the user to adjust the depths of the displayed image.

In an embodiment, markings correspond to one or more rows segmented on the touchpad indicating corresponding depths of the image being adjusted by the user using the one or more rows of the touchpad.

The touchpad 110 of an embodiment of the present invention combines the functionality of a trackball and TGC potentiometers functionality used in traditional ultrasound scanners; hence, a cost advantage and system simplification is obtained.

In an embodiment, the touchpad 110 can be controlled using software. The number of regions is not limited and hence provides users with more accurate adjustments if needed.

In an embodiment, it is possible to memorize (pre-set) several different TGC settings for different applications by the processor 114 using a touchpad having one or more rows (sliders) and display unit 112 having markings corresponding to depths of the image.

In an embodiment, the touchpad 110 is able to automatically remap and create any number of sliders, have memory settings of TGC, and draw any desired TGC curve shape itself to implement the desired gain variation. Commercially, it provides product differentiation, simplification, low cost and ability to build systems for harsh conditions.

An embodiment of the present invention allows implementation of TGC functionality on a separate touch screen or touch screen attached to monitor.

An ultrasound device to implement Time Gain Compensation (TGC) is disclosed as an embodiment of the present invention. The ultrasound device comprises an input unit and a display unit. The input unit comprises a touchpad. The touchpad is segmented into one or more rows, wherein each row is mapped to a corresponding depth of an image which is formed based on echoed signals of an object received through an ultrasound probe. The one or more rows on the touchpad enables a user to adjust gain of the image using Time Gain Compensation (TGC) functionality implemented in a processor associated with the ultrasound device. The display unit comprises at least one predetermined marking corresponding to one or more rows segmented on the touchpad. The at least one marking on the display unit indicates a corresponding depth of the image being adjusted by the user using the one or more rows of the touchpad.

A method of processing an image using ultrasound device is also disclosed as an embodiment of the present invention. The method comprises receiving echoed signals of an object through an ultrasound probe by a processor and forming an image based on echoed signals of the object. Then, depths of the image before displaying on a display unit are computed by the processor. The computed depths of the image are mapped to one or more corresponding rows formed on a touchpad. This touchpad enables a user to adjust gain of the image using Time Gain Compensation (TGC) function implemented in the processor.

This written description uses examples to disclose embodiments of the invention, including the best mode, and also to enable any person skilled in the art to practice the invention, including making and using any devices or systems and performing any incorporated methods. The patentable scope of embodiments of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An ultrasound device comprising:
an input unit comprising a touchpad with multi-touch support segmented into at least one row, wherein each row is mapped to a corresponding depth of an image formed based on echoed signals of an object received through an ultrasound probe, and wherein the touchpad enables a user to adjust gain of the image using a Time Gain Compensation (TGC) function implemented in a processor associated with the ultrasound device; and
a display unit comprising at least one predetermined marking corresponding to at least one row segmented on the touchpad, wherein the at least one predetermined marking indicates a corresponding depth of the image being adjusted by the user using at least one row of the touchpad.

2. The ultrasound device as in claim 1, wherein the depth of the displayed image is about 1 centimeter to about 30 centimeters.

3. The ultrasound device as in claim 1, wherein the gain of the image is brightness, wherein the brightness is manipulated as per a gain curve shape indicated by a finger placed across the touchpad with multi-touch support.

4. The ultrasound device as in claim 1, wherein the gain of a desired depth of the image is adjusted by sliding at least one of a finger and a stylus horizontally across the row of the touchpad mapped with the corresponding desired depth of the image.

5. The ultrasound device as in claim 1, wherein the object is selected from at least one of a human body and an animal body.

6. A method of processing an image using an ultrasound device, the method comprising:
   receiving an echoed signal of an object through an ultrasound probe by a processor and forming an image based on the echoed signals of the object;
   computing depths of the image before displaying on a display unit by the processor;
   mapping the depths of the image to one or more corresponding rows formed on a touchpad, each row mapped to a corresponding depth of the image formed based on echoed signals of the object received through the ultrasound probe; and
   adjusting the gain of the image using a Time Gain Compensation (TGC) function implemented in the processor by moving at least one of a finger and a stylus in a predefined direction on the touchpad, mapped correspondingly to a desired depth of the image.

7. The method as in claim 6, wherein the depth of the displayed image is about 1 centimeter to about 30 centimeters.

8. The method as in claim 6, wherein a shape of an applied TGC curve is displayed next to the image for reference.

9. The method of claim 6, wherein the display unit comprises at least one predetermined marking corresponding to at least one of the one or more rows formed on the touchpad, wherein the at least one predetermined marking indicates a corresponding depth of the image being adjusted by a user using at least one of the one or more rows of the touchpad.

* * * * *